United States Patent [19]

Casareto et al.

[11] Patent Number: 5,747,330
[45] Date of Patent: May 5, 1998

[54] ANTIBIOTIC PRODUCING MICROBE

[75] Inventors: Enrico Casareto, Verona; Massimo Leoni; Enrico Ronzio, both of Milan; Ambrogio Magni, Osnago CO, all of Italy

[73] Assignee: Poli Industria Chimica, Italy

[21] Appl. No.: 658,653

[22] Filed: Jun. 5, 1996

[51] Int. Cl.$^6$ .................... C12N 1/14; C12P 21/04
[52] U.S. Cl. .............. 435/254.1; 435/71.1; 435/71.3; 435/171; 435/911; 514/11; 530/321
[58] Field of Search .................... 435/71.1, 71.3, 435/171, 254.1, 911; 530/321; 514/11

[56] References Cited

U.S. PATENT DOCUMENTS

| | | | |
|---|---|---|---|
| 4,117,118 | 9/1978 | Härri et al. | 424/177 |
| 4,215,199 | 7/1980 | Härri et al. | 435/71 |
| 4,220,641 | 9/1980 | Traber et al. | 424/177 |
| 4,289,851 | 9/1981 | Traber et al. | 435/71 |
| 4,384,996 | 5/1983 | Bollinger et al. | 530/321 |
| 4,639,434 | 1/1987 | Wenger et al. | 514/11 |
| 5,156,960 | 10/1992 | Jekkel née Bokány et al. | 435/71.1 |
| 5,256,547 | 10/1993 | Rudat et al. | 435/71.1 |
| 5,318,901 | 6/1994 | Patchett et al. | 435/71.1 |
| 5,409,816 | 4/1995 | Lundell et al. | 435/713 |
| 5,447,854 | 9/1995 | Goto et al. | 435/71.3 |

FOREIGN PATENT DOCUMENTS

| | | |
|---|---|---|
| WO 96/12031 | 4/1996 | WIPO . |
| WO 96/12032 | 4/1996 | WIPO . |

OTHER PUBLICATIONS

C. E. Isaac et al., Production of Cyclosporins by Tolypocladium niveum Strains, *Antimicrobial Agents and Chemotherapy* 34, No. 1:121–127 (1990).

*Primary Examiner*—Herbert J. Lilling
*Attorney, Agent, or Firm*—Townsend and Townsend and Crew LLP

[57] ABSTRACT

A novel, cyclosporin-producing microbe is described. A process for the production of cyclosporin, comprising culturing the novel microbe and recovering the desired form of cyclosporin produced, is described.

1 Claim, 8 Drawing Sheets

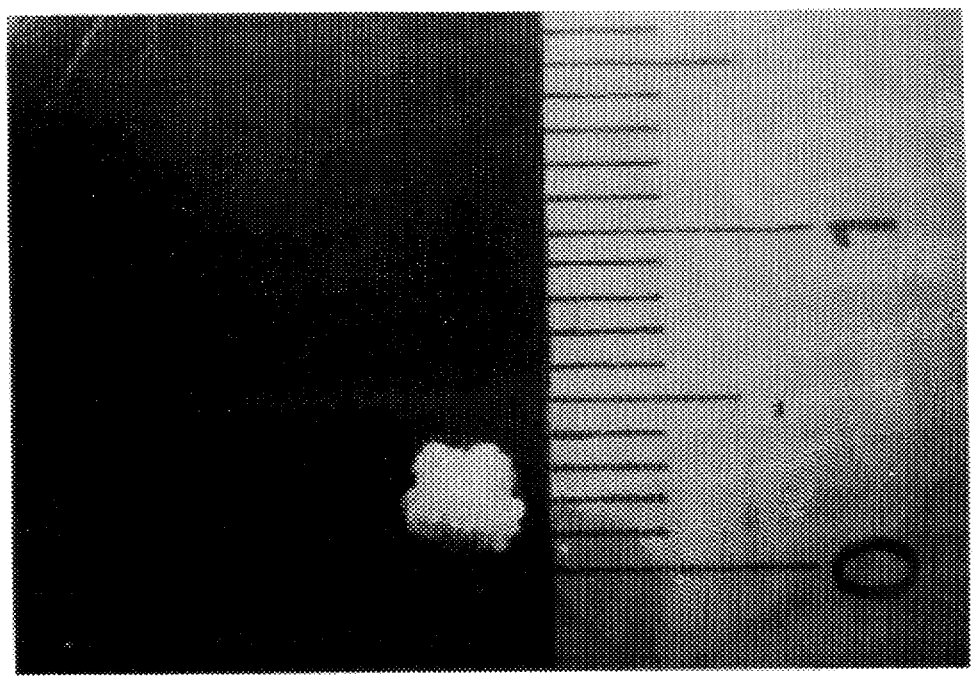
FIG. IA

```
SAMPLE   1   CYCS13B1   BIN  9   NAME   ARUN0009
   SA      IS     XF
   27.5    0     74.5
```

| NAME | mcg/ml | RT | AREA | BC | RF | |
|---|---|---|---|---|---|---|
| 1 | 0.712 | 3.94 | 4178 | 01 | 15899.734 | |
| 2 | 21.286 | 4.11 | 124931 | 03 | 15899.734 | |
| 3 | 4.056 | 4.6 | 23803 | 01 | 15899.734 | |
| 4 | 0.65 | 4.88 | 3815 | 02 | 15899.734 | |
| 5 | 6.553 | 5.14 | 38460 | 03 | 15899.734 | |
| 6 | 1.637 | 5.6 | 9606 | 01 | 15899.734 | |
| 7 | 35.318 | 6.09 | 207285 | 01 | 15899.734 | |
| 8 | 9.726 | 7.02 | 57079 | 01 | 15899.734 | |
| 9 | 3.173 | 7.96 | 18621 | 02 | 15899.734 | |
| 10 | 2.533 | 8.37 | 14871 | 03 | 15899.734 | |
| 11 | 3.738 | 9.45 | 21936 | 01 | 15899.734 | |
| 12 | 3.764 | 10.5 | 22091 | 01 | 15899.734 | |
| 13 | 3.979 | 12.07 | 23355 | 02 | 15899.734 | |
| 14 | 3.625 | 12.55 | 21272 | 03 | 15899.734 | |
| 15 | 6.379 | 15.05 | 37443 | 02 | 15899.734 | |
| 16 | 3.611 | 15.59 | 21193 | 03 | 15899.734 | |
| 17 | 8.554 | 17.35 | 50201 | 02 | 15899.734 | |
| 18 | 11.735 | 18.26 | 68872 | 02 | 15899.734 | |
| 19 | 23.898 | 18.71 | 140260 | 03 | 15899.734 | |
| 20 | 579.379 | 20.58 | 3400390 | 08 | 15899.734 | ← CYCLOSPORIN C |
| 21 | 3.262 | 21.31 | 19148 | 05 | 15899.734 | |
| 22 | 17.741 | 22.71 | 104123 | 01 | 15899.734 | |
| 23 | 545.328 | 24.61 | 3200541 | 02 | 15899.734 | ← CYCLOSPORIN B |
| 24 | 17.826 | 26.02 | 104626 | 02 | 15899.734 | |
| 25 | 59.788 | 27.11 | 350898 | 08 | 15899.734 | |
| 26 | 25.322 | 29.06 | 148619 | 06 | 15899.734 | |
| 27 | 12.095 | 30.15 | 70987 | 06 | 15899.734 | |
| CYCA | 3014.026 | 31.967 | 17689407 | 08 | 15899.734 | ← CYCLOSPORIN A |
| 29 | 40.068 | 34.57 | 235161 | 05 | 15899.734 | |
| 30 | 16.613 | 38.85 | 97498 | 02 | 15899.734 | |
| 31 | 40.238 | 41.73 | 240266 | 02 | 15899.734 | |
| 32 | 120.718 | 44.13 | 708468 | 03 | 15899.734 | ← CYCLOSPORIN D |
| 33 | 24.755 | 52.71 | 145290 | 01 | 15899.734 | |
| 34 | 25.138 | 58.09 | 147537 | 01 | 15899.734 | |

TOTALS  4697.919              27572226

FIG. 3B.

SAMPLE 1 SNUZ          BIN 3 NAME ARUN0003
  SA    IS    XF
  27.5  0     73.5

| | | | | | |
|---|---|---|---|---|---|
| 1 | 28.813 | 3.57 | 168086 | 01 | 15592.097 |
| 2 | 42.947 | 4.37 | 250544 | 01 | 15592.097 |
| 3 | 4.934 | 5.14 | 58788 | 01 | 15592.097 |
| 4 | 7.905 | 5.71 | 46170 | 01 | 15592.097 |
| 5 | 7.213 | 6.33 | 42084 | 01 | 15592.097 |
| 6 | 20.67 | 7.42 | 120582 | 02 | 15592.097 |
| 7 | 3.897 | 7.72 | 22732 | 03 | 15592.097 |
| 8 | 6.841 | 8.49 | 39908 | 01 | 15592.097 |
| 9 | 0.71 | 9.23 | 4143 | 02 | 15592.097 |
| 10 | 4.632 | 9.63 | 27025 | 02 | 15592.097 |
| 11 | 2.584 | 10.07 | 15073 | 08 | 15592.097 |
| 12 | 0.264 | 10.54 | 1538 | 05 | 15592.097 |
| 13 | 0.72 | 11.46 | 4303 | 02 | 15592.097 |
| 14 | 5.191 | 11.85 | 30285 | 02 | 15592.097 |
| 15 | 2.23 | 12.81 | 13005 | 02 | 15592.097 |
| 16 | 2.476 | 13.37 | 14446 | 02 | 15592.097 |
| 17 | 2.091 | 13.8 | 12201 | 02 | 15592.097 |
| 18 | 5.571 | 14.37 | 32495 | 03 | 15592.097 |
| 19 | 2.035 | 16.17 | 11876 | 01 | 15592.097 |
| 20 | 3.554 | 17.44 | 20733 | 02 | 15592.097 |
| 21 | 10.237 | 17.98 | 59718 | 02 | 15592.097 |
| 22 | 29.355 | 19.02 | 171253 | 03 | 15592.097 ← CYCLOSPORIN C |
| 23 | 5.992 | 20.89 | 34954 | 02 | 15592.097 |
| 24 | 6.892 | 21.85 | 40207 | 02 | 15592.097 |
| 25 | 33.671 | 22.58 | 196427 | 03 | 15592.097 ← CYCLOSPORIN B |
| 26 | 0.971 | 23.85 | 5666 | 02 | 15592.097 |
| 27 | 7.936 | 24.87 | 46297 | 02 | 15592.097 |
| 28 | 8.634 | 26.12 | 50372 | 03 | 15592.097 |
| CYCA | 385.065 | 29.16 | 2246382 | 02 | 15592.097 |
| 30 | 9.045 | 31.11 | 52767 | 02 | 15592.097 |
| 31 | 5.693 | 34.05 | 33208 | 02 | 15592.097 ← CYCLOSPORIN A |
| 32 | 21.739 | 35.91 | 126821 | 02 | 15592.097 |
| 33 | 78.59 | 37.38 | 458476 | 03 | 15592.097 ← CYCLOSPORIN D |
| TOTALS | 759.108 | | 4428465 | | |

FIG. 4B.

ANTIBIOTIC PRODUCING MICROBE

FIELD OF THE INVENTION

The present invention relates to a novel cyclosporin-producing microbe, apparently a member of the fungal genus Tolypocladium, and to a process for producing cyclosporins by the fermentation of this microbe.

BACKGROUND OF THE INVENTION

Cyclosporins are a group of non-polar cyclic oligopeptide compounds having immunosuppressant activity. Cyclosporins are produced by fungal fermentation. Cyclosporins have been employed for several years to combat rejection of transplanted organs and tissues in humans. Recently, investigators have been seeking additional therapeutic applications for the drug.

At least nine different cyclosporins are produced by the fungi, including cyclosporin A, B, C, D, E, F, G, H, and I, all having varying amino acid composition. Cyclosporin A is the major component and currently enjoys the most widespread clinical use. See, e.g., Ruegger et al., *Helv. Chim. Acta* 59:1075 (1976); Traber et al., *Helv. Chim. Acta* 60:1568 (1977); Rehacek and De-xiu, *Process Biochem* 26:157 (1991). Cyclosporin A is commercially available under the tradename SANDIMMUNE® from Sandoz Corp.

Cyclosporins were originally isolated as metabolites produced by fungal strains of *Cylindrocarpon lucidum* Booth and *Tolypocladium inflatum* Gams (Gams, *Persoonia* 6:185 (1971)), isolated from soil samples from the United States of America and Norway. *T. inflatum* is also known as *Tolypocladiumn niveum*. Isaac et al., *Antimicro. Agents Chemother.* 34:121 (1990). (The genus Tolypocladium was first described by Gams, *Persoonia*, 6:185 (1971); the genus name Beauveria has been used synonymously with Tolypocladium.) Species of Tolypocladium are typically slow in growth and form white, flocculent colonies with a large amount of spores.

A production strain of Tolypocladium (*Tolypociadium inflatum* (NRRL 8044)) was at first identified as *Trichoderma polysporum* (Link ex Pers) Rifai. The use of this strain for the production of antibiotic substances is described in Finnish Patent No. 54606. Growth conditions and taxonomy of this production strain are provided in Dreyfuss et al., *Eur. J. Appl. Microbiol.* 3:125 (1976).

Other cyclosporin producing strains are described in Finnish Patent No. 52851 (*Cylindrocarpon lucidum* Booth (NRRL 5760)), German patent 298276 (*Tolypocladium inflatum* strain SF 136), Great Britain patent 2,227,489 (*Tolypocladium varium*), Japan patent 826 3093 (two strains of cyclosporin producing Fusarium), and U.S. Pat. No. 5,409,816 (Tolypocladium sp. LEA3). However, not all strains of Tolypocladium species are cyclosporin producing. Isaac et al. (1990).

Cyclosporin production varies among species and strains, and production processes for cyclosporin A have encountered problems with low yields or the need for long fermentation times. Even where a microbial strain has been shown to produce relatively high yields of cyclosporin, the relative amount of cyclosporin produced often is small. Dexiu et al., *Folia Microbiol.* 36:549–556 (1991). The cyclosporin production of some known strains of Tolypocladium are compared in Isaac et al., *Antimicro. Agents Chemother.* 34:121 (1990). Of the nine cyclosporin producing strains compared in Isaacs et al., total cyclosporin production (forms A, B and C) after 10–15 days of growth ranged from 12 mg/liter to 123 mg/liter, using their described production process. A mutant of *T. inflatum* NRRL 8044 is described as producing about 500 mg of Cyclosporin A per liter in Traber et al., *J. Antibiotics* 42:591 (1989). Slight improvements in yield have been reported using selected amino acids or carbon sources, however, the operating expense of such methods renders them unsuitable for large-scale commercial use. See, e.g., Agathos et al., *Ann. NY Acad. Sci.* 506:657 (1987); Kobel et al. *Europ. J. Appl. Microbiol. Biotechnol.* 14:237 (1982). Accordingly, it is desirable to identify new strains of cyclosporin-producing microbes which can be used efficiently in the production of cyclosporins.

SUMMARY OF THE INVENTION

It is an object of the present invention to provide a productive cyclosporin-producing microbe.

It is a further object of the present invention to provide a biologically pure culture of a productive cyclosporin-producing microbe having the identifying characteristics of the deposit having provisional accession number I-1714, made in accordance with the provisions of the Budapest Treaty on 28 May 1996, with the Collection Nationale de Cultures de Microorganisms, Institut Pasteur, 25 Rue du Docteur Roux, Paris.

Another object of the present invention is a process for producing cyclosporin, wherein a microbe strain having all of the identifying characteristics of the deposit having provisional accession number I-1714 (Collection Nationale de Cultures de Microorganisms, Institut Pasteur, Paris) and referred to herein as Tolypocladium sp. (Poli) is aerobically fermented in a nutrient medium containing a carbon source utilizable by the microbe strain until cyclosporin is produced, and the cyclosporin produced is recovered.

The foregoing and other objects and aspects of the present invention are explained in detail in the specification set forth below.

BRIEF DESCRIPTION OF THE DRAWINGS

FIG. 1A is a photograph of a colony of one strain of Tolypocladium sp. (Poli).

FIG. 3B is a chart tabulating the data represented in the chromatograph of FIG. 3A.

FIG. 4B is a chart tabulating the data represented in the chromatograph of FIG. 4A.

DETAILED DESCRIPTION OF THE INVENTION

Figure 1B:
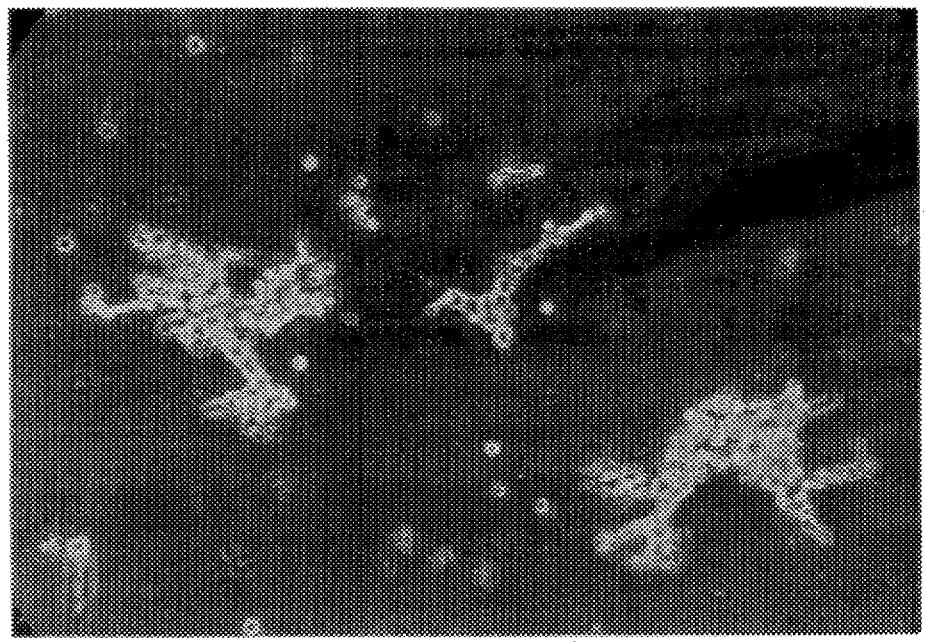
FIG. 1B is a photograph showing the morphology of a strain of Tolypocladium sp. (Poli).

The novel microbe described herein provides a high yield of cyclosporin within a relatively short fermentation time, and is referred to herein as Tolypocladium sp. (Poli). This novel microbe was isolated from a soil sample obtained in Russia. The original isolate initially obtained from the soil sample possessed the general characteristics of the fungal genus Tolypocladium (as described in Gams, *Persoonia* 6:185 (1971) and Bissett, *Can. J. Bot.* 61:1311 (1983)): short cylindrical conidiophores with terminal and lateral phialides, ellipsoidal to subglobose basally and narrowing into a cylindrical neck, often crooked, and bearing subglobose conidia. This original strain produced a low yield of cyclosporin antibiotic complex. After repeated mutagenesis and selection a new microbial strain was isolated with a distinct macroscopic appearance of the colonies and distinct biochemical characteristics. This strain is termed Tolypocladium sp. (Poli), and pure cultures have been grown. Specimens of Tolypocladium sp. (Poli) have been deposited on 28 May, 1996 according to the Budapest Treaty at the Collection Nationale de Cultures de Microorganismes, Institute Pasteur, 25 Rue du Docteur Roux, Paris, France (accession number I-1714).

The novel microbe described herein is referred to as Tolypocladium sp. (Poli) and, while not wishing to be limited to a single theory of taxonomy, the data suggest that this microbe is a novel species of Tolypocladim. The novel microbe of the present invention possesses all of the general characteristics of the genus Tolypocladium yet is distinct from *Tolypocladiumn inflatum* (Gams) in morphology and in cyclosporin production. Alternatively, the novel microbe of the present invention may be termed a distinct strain of *Tolypocladium inflatum*.

Tolypocladium sp. Poli was compared to various species and strains of cyclosporin-producing microbes to establish its distinct characteristics. Tolypocladium Sp. (Poli) is slow-growing, forming cream colored colonies from 3–8 mm in diameter, with a wrinkled appearance when grown for 15 days at 24° C. on a solid medium containing Beet molasses (1.5%), glycerol (1.5%), peptone (0.6%), sodium chloride (0.5%) and other mineral salts and trace elements. The vegetative hyphae are composed of chains of swollen cells, and spore-forming ability is weak. Conidiophores are hyaline, cylindrical, usually arising as short, irregular branches from the aerial mycelium. Phialides are solitary or in verticils, ellipsoidal to subglobose basally, and narrowing abruptly into a cylindrical neck of variable length. The phialides become elongated toward the end of their development.

Tolypocladium sp. (Poli) can efficiently utilize the following as carbon sources: cellobiose, maltose, trehalose, galactose, glycerol, melezitose, sucrose, sorbitol, D-xylose, dextrin, and fructose. The following can also be utilized as carbon sources by Tolypocladium sp. (Poli), although less efficiently: mannitol and glucosamine. None of the following are utilized by Tolypocladium sp. (Poli) as a carbon source: L-arabinose, inositol, lactose, raffinose, xylitol, lactulose, stachyose, D-tagatose.

Tolypocladium sp. (Poli) can utilize either organic or inorganic nitrogen sources, including but not limited to corn steep liquor; dry yeast; protein hydrolysates (peptones) derived from casein, liver, lactalbumen, yeast, blood, meat and soya; vegetable meals (soya bean, cotton seed, corn gluten); urea and ammonium salts (nitrates, phosphates, sulphates).

Tolypocladium sp. (Poli) may be cultivated on various nutrient media containing the typical nutrients for fungi, including a carbon source suitable for (i.e., utilizable by) the microbe, a nitrogen source, and mineral salts and trace elements as are known in the art. As used herein, a medium capable of supporting Tolypocladium sp. (Poli) is one which contains a carbon source utilizable by the microbe and a nitrogen source utilizable by the microbe. Such a medium may be natural, synthetic or semisynthetic. Numerous compositions useful as carbon sources and nitrogen sources in culture media are well known in the art. In addition, inorganic salts may be added to the culture medium as necessary, as is known in the art.

In a process according to the present invention for the production of cyclosporins, and particularly cyclosporin A, Tolypocladium sp. (Poli) is first cultured aerobically for 48–72 hours in a growth medium containing carbon and nitrogen sources utilizable by Tolypocladium sp. (Poli) at temperatures from about 200° C. to about 30° C., preferably at about 24–250° C. The growth medium is inoculated with a suspension of conidia and/or mycelia from Tolypocladium sp. (Poli). A fraction of this initial culture, such as 10–20%, is then used to inoculate a production medium containing carbon and nitrogen sources utilizable by the microbe. Precursor amino acids may be added to the medium in order to improve the production of cyclosporin or to vary the relative amounts of the different cyclosporins, as is known in the art and as would be apparent to one skilled in the art. Aerobic fermentation is carried out at temperatures of from about 20° C. to about 25° C. (preferably at about 24° C.) for times of from about 8 to about 11 days. Commercially available fermentation devices may be used in the present process, as would be apparent to one of ordinary skill in the art. Cyclosporin production may be monitored using methods known in the art including, for example, measurement of antifungal activity of the culture broth or chromatographic analysis. Fermentation is stopped when a maximum or desired cyclosporin production is obtained. The desired cyclosporins are then recovered from the culture broth using methods known in the art and purified as needed. See, e.g., U.S. Pat. No. 4,215,199; U.S. Pat. No. 5,156,960.

Use of the novel microbe of the present invention, here termed Tolypocladium sp. (Poli), according to the present invention provides a high yield of cyclosporin antibiotic complex. Yields of up to 1.5 g/L, 2.0 g/L, and even 3.0 g/L and above may be obtained. The cyclosporin produced by Tolypocladium sp. (Poli) contains cyclosporin A as the main product (more than 50%), and contains cyclosporins B, C and D as minor components. Up to 60%, 70% and even 80% or more of cyclosporin A may be obtained. The relative amounts of the different cyclosporins may be varied somewhat by maintaining the pH of the culture at different values between pH 3–pH 7, such as by adding a diluted ammonia solution (as would be apparent to one skilled in the art).

An advantageous cyclosporin producing process is described in the co-pending United States patent application of B. Bocchiola, V. Buran and A. Magni, filed concurrently herewith.

The following examples are provided to illustrate the present invention, and should not be construed as limiting thereof. In these examples, g means gram, L means liter, mL means milliLiter, rpm means revolutions per minute, VVM means volume of air per unit volume of fermentation broth per minute, °C. means degrees centigrade, and mcg means microgram.

EXAMPLE 1

Carbon Sources

The ability of *Tolypocladium inflatum* ATCC 34921 (NRRL 8044) and Tolypocladium sp. (Poli) to utilize varied carbon sources was directly compared by growing cultures under identical conditions. The ability of Tolypocladium sp. LEA3 (U.S. Pat. No. 5,409,816) to utilize various carbon sources was obtained from published sources.

*Tolypocladium inflatum* ATCC 34921 (NRRL 8044) and Tolypocladium sp. (Poli) strains were compared in side-by-side growth tests using a liquid semi-synthetic medium containing corn steep powder (1 g/L), urea (1 g/L) and mineral salts (2 g/L $KH_2PO_4$; 3 g/L NaCl; 0.5 g/L $MgSO_4$; 1 g/L $NaNO_3$; 0.5 g/L KCl; 0.015 g/L $FeSO_4$; 0.003 g/L $MnSO_4$; 0.003 $ZnSO_4$; 0.001 $CuSO_4$) with different carbon sources added to a final concentration of 30 g/L. Shake flasks containing 25 mL of medium were inoculated with a suspension of conidia and mycelia and incubated for 4 days at 24° C. on a gyratory shaker at 240 rpm. Growth was assessed by measuring the dry weight in each flask after 4 days, compared with a control flask containing the same medium without a carbon source, inoculated with the same suspension.

Information provided in Table 1 regarding Tolypocladium sp. LEA3 was obtained from U.S. Pat. No. 5,409,816.

As shown in Table 1, Tolypocladium sp. (Poli) was unable to use L-arabinose, inositol, and xylitol, whereas Tolypocladium sp. LEA3 was able to utilize each of these compounds as a carbon source. In contrast to T. inflatum ATCC 34921 (NRRL 8044), T. (Poli) was unable to use inositol or xylitol as a carbon source.

TABLE 1

| Carbon Source | Tolypocladium sp. (LEA3) | Tolypocladium sp. (Poli) | T. inflatum ATCC 34921 (NRRL 8044) |
|---|---|---|---|
| Control | − | − | − |
| L-arabinose | + | − | − |
| Cellobiose | + | + | + |
| Inositol | + | − | +/− |
| Lactose | − | − | − |
| Maltose | + | + | + |
| Raffinose | − | − | − |
| Trehalose | + | + | + |
| Xylitol | + | − | + |
| Galactose | + | + | + |
| Glycerol | + | + | + |
| Melezitose | + | + | + |
| Sucrose | + | + | + |
| Sorbitol | + | + | + |
| D-Xylose | + | + | + |
| Dextrin | (nd) | + | + |
| Fructose | (nd) | + | + |
| Mannitol | (nd) | +/− | + |
| Glucosamine | (nd) | +/− | +/− |
| Lactulose | (nd) | − | − |
| Stachyose | (nd) | − | (nd) |
| D-tagatose | (nd) | − | (nd) |

(−) indicates a dry weight of <1 g/L
(+/−) indicates a dry weight of between 1 and 2 g/L
(+) indicates a dry weight of >2 g/L
(nd) indicates this test was not done

EXAMPLE 2

Comparison of Colony Growth and Fungal Morphology

The growth and characteristics of colonies of Tolypocladium sp. (LEA3), Tolypocladium inflatum ATCC 34921 (NRRL 8044), and Tolypocladium sp. (Poli) were compared, as was fungal morphology.

Fungal morphology of *Tolypocladium inflatum* ATCC 34921 (NRRL 8044) and Tolypocladium sp. (Poli) were compared after growth under identical conditions: microbes were grown directly on a sterile microscope slide, partially submerged in a liquid medium containing glucose (1.5%), glycerol (3%), yeast extract (0.5%), $KH_2PO_4$ (0.5%) and NaCl (0.5%) at room temperature. After 5 and 10 days the aerial mycelium were observed using a microscope. Description of Tolypocladium sp. (LEA3) was obtained from the published literature. Results are provided in Table 3.

Table 2 compares additional characteristics of the three microbe strains. Tolypocladium sp. (Poli) can be distinguished from each of the other two strains as shown, for example, by comparing colony appearance, the forms of cyclosporin produced, and morphology. Growth was assessed subjectively using visual inspection and measurement. Colonies of *Tolypocladium inflatum* ATCC 34921 (NRRL 8044), when grown on a solid medium, are visible after 4–5 days while colonies of Tolypocladium sp. (Poli) are visible after one week. When these two microbial strains are grown in the same conditions using a liquid medium containing a suitable carbon source and identical inoculum, the growth curve obtained by plotting the dry weight values at different times are different, with *Tolypocladium inflatum* ATCC 34921 (NRRL 8044) growing faster than Tolypocladium sp. (Poli).

TABLE 2

| | Growth | Cyclosporins | Spore-forming Ability | Colony Appearance | Odor | Hyphae Morphology |
|---|---|---|---|---|---|---|
| T. inflatum NRRL 8044 | rapid | A B C D | Strong | white, floccose, unwrinkled | indistinct | hyaline, thin, elongated and branched |
| Tolypocladium (Poli) | slow | A B C D | Weak | cream, wrinkled | indistinct | swollen cells, chains |
| T. sp LeA3 | rapid | A B C D G | Weak | greyish | indistinct | swollen cells, chains |

Growth of Poli and NRRL 8044 was assessed by visual inspection and measurement; "rapid" and "slow" are comparative assessments.
Spore-forming ability of Poli and NRRL 8044 was assessed visually using a microscope.
Colony appearance of Poli and NRRL 8044 was assessed by visual, side-by-side comparison.

TABLE 3

|  | Conidiophore Morphology | Phialides Morphology | Conidia Morphology |
|---|---|---|---|
| T. inflatum NRRL 8044 (ATCC 34921) | hyaline, cylindrical, usually arising as short branches from the aerial mycelium, irregularly branched | solitary or in verticils, ellipsoidal to subglobose basally, narrowing abruptly into a cylindrical neck with varied length, frequently bowed; become elongated at the end of their development | description not possible |
| Tolypocladium (Poli) | hyaline, cylindrical, usually arising as short branches from the aerial mycelium, irregularly branched | solitary or in verticils, ellipsoidal to subglobose basally, narrowing abruptly into a cylindrical neck with varied length, frequently bowed; become elongated at the end of their development | description not possible |
| T. sp LeA3 | not described | not described | irregular |

Figure 2A:
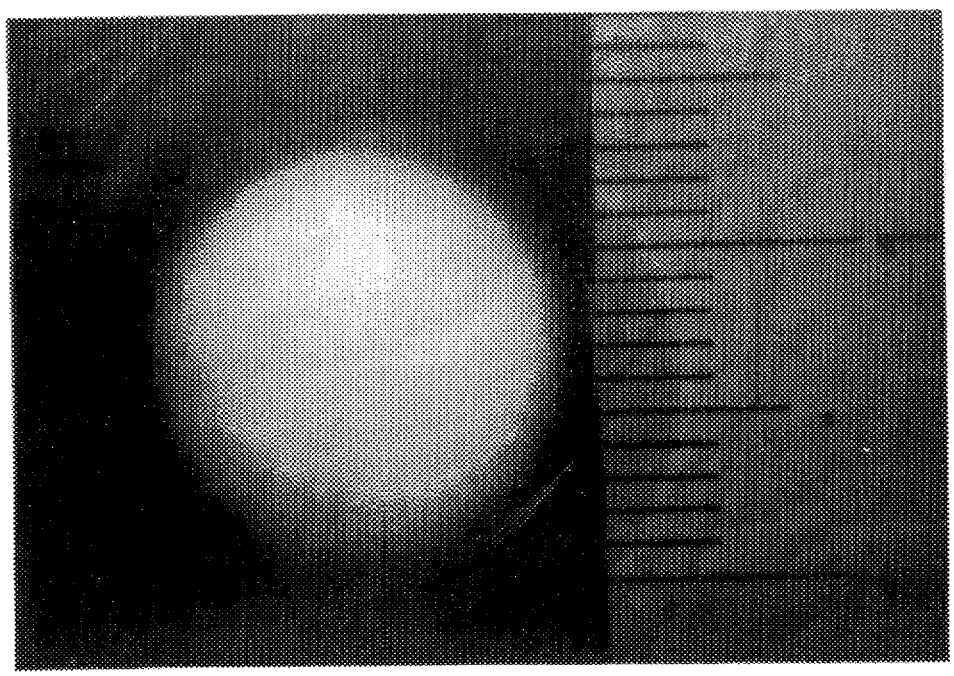
FIG. 2A is a photograph of a colony of *Tolypocladium inflatum* ATCC 34921 (NRRL 8044).
Figure 2B:
FIG. 2B is a photograph showing the microscopic morphology of *Tolypocladium inflatum* ATCC 34921 (NRRL 8044).

A colony of one strain of Tolypocladium sp. (Poli) is shown in FIG. 1A; a colony of *Tolypocladium inflatum* ATCC 34921 (NRRL 8044) is shown in FIG. 2A for comparison. FIG. 1B is a photograph showing the morphology of a strain of Tolypocladium sp. (Poli); FIG. 2b is a photograph showing the microscopic morphology of *Tolypocladium inflatumn* ATCC 34921 (NRRL 8044).

EXAMPLE 3

Cyclosporin Production by Tolypocladium sp. (Poli)

Tolypocladium sp (Poli), as described above, was cultured and the production of cyclosporin was assessed. The microbe was cultured using a seed medium containing sucrose and a production medium containing glucose was utilized. Cyclosporin A was separated from other forms of cyclosporin and other fermentation byproducts using chromatography. Using identical methods, Tolypocladium sp NRRL 8044 (ATCC 34921) was cultured and the production of cyclosporin was assessed.

Growth and fermentation were carried out as follows: A shake flask of 2000 mL capacity was filled with 500 mL of a seed medium containing 2% sucrose, 1.5% glycerol, 0.7% ammonium sulfate, 0.5% sodium chloride and 0.2% potassium phosphate. Flasks were inoculated with a suspension of mycelium and conidia obtained from a piece of a 14–20 day old agar slant culture, chopped in 6–10 mL of water. Flasks were incubated for 2–3 days at 20° C. to 30° C. (preferably at 24° C.) on an alternative shaker. Flasks were then used to inoculate a fermentor of 10 L capacity, filled with 5 L of the same seed medium. The seed culture was cultivated for 2–3 days at 20° C. to 30° C. (preferably at 24° C.), and used as inoculum for the production medium (composed of glucose, glycerol, peptone, urea, sodium nitrate, ammonium sulfate, potassium phosphate, and other mineral salts and trace elements as are known in the art). In a convenient method, a 10% to 20% v/v of the seed culture was transferred in the production medium. Fermentation was performed at 20° C. to 25° C. (preferably at 24° C.) for 10–14 days. The aerobic conditions were maintained by stirring (60 to 120 rpm) and aerating the broth at 0.5 to 1 VVM (volume of air per unit volume of fermentation broth per minute).

Figure 3A:
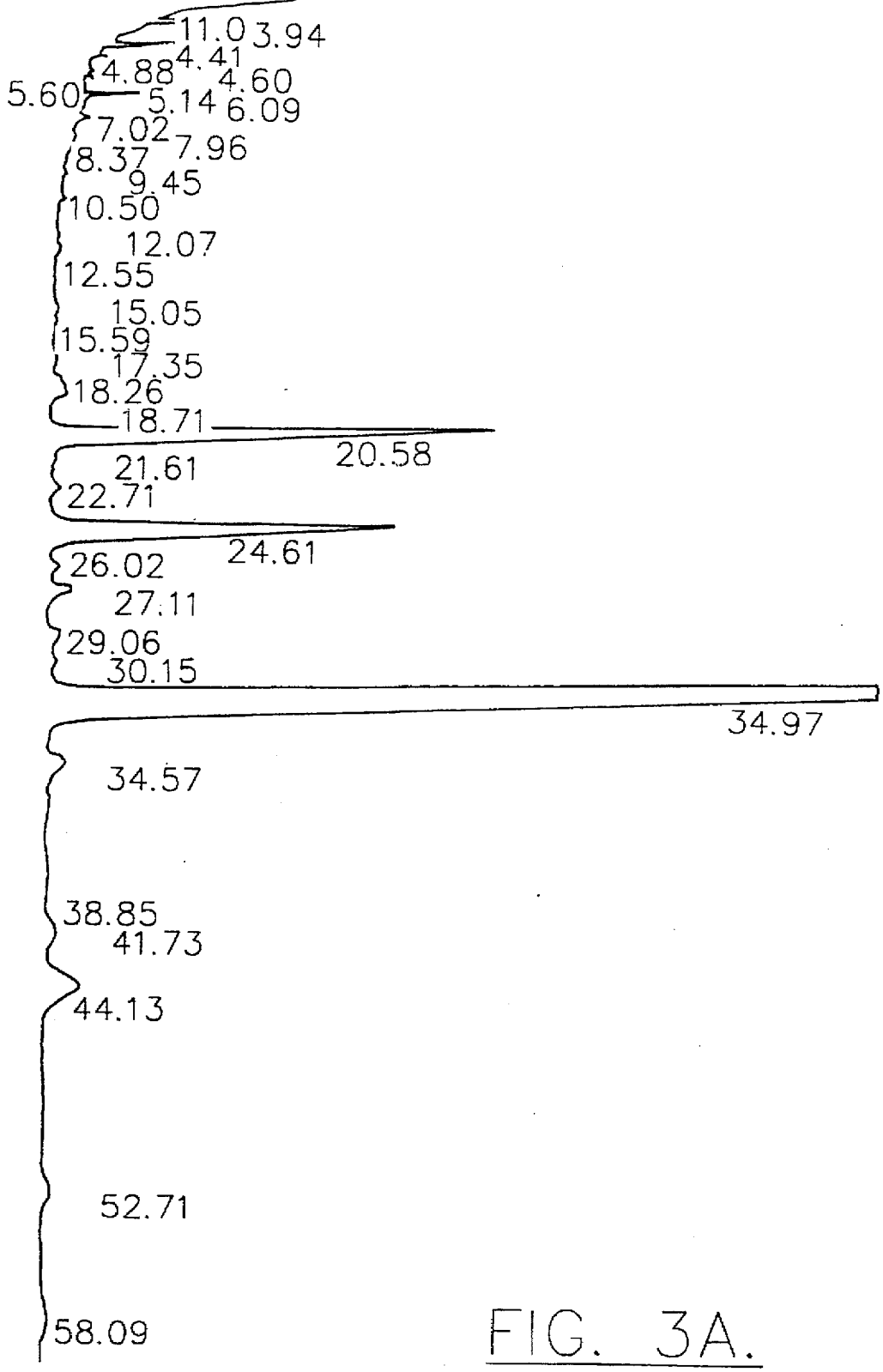
FIG. 3A is a chromatograph showing the production of cyclosporin by fermentation of Tolypocladium sp (Poli).
Figure 4A:
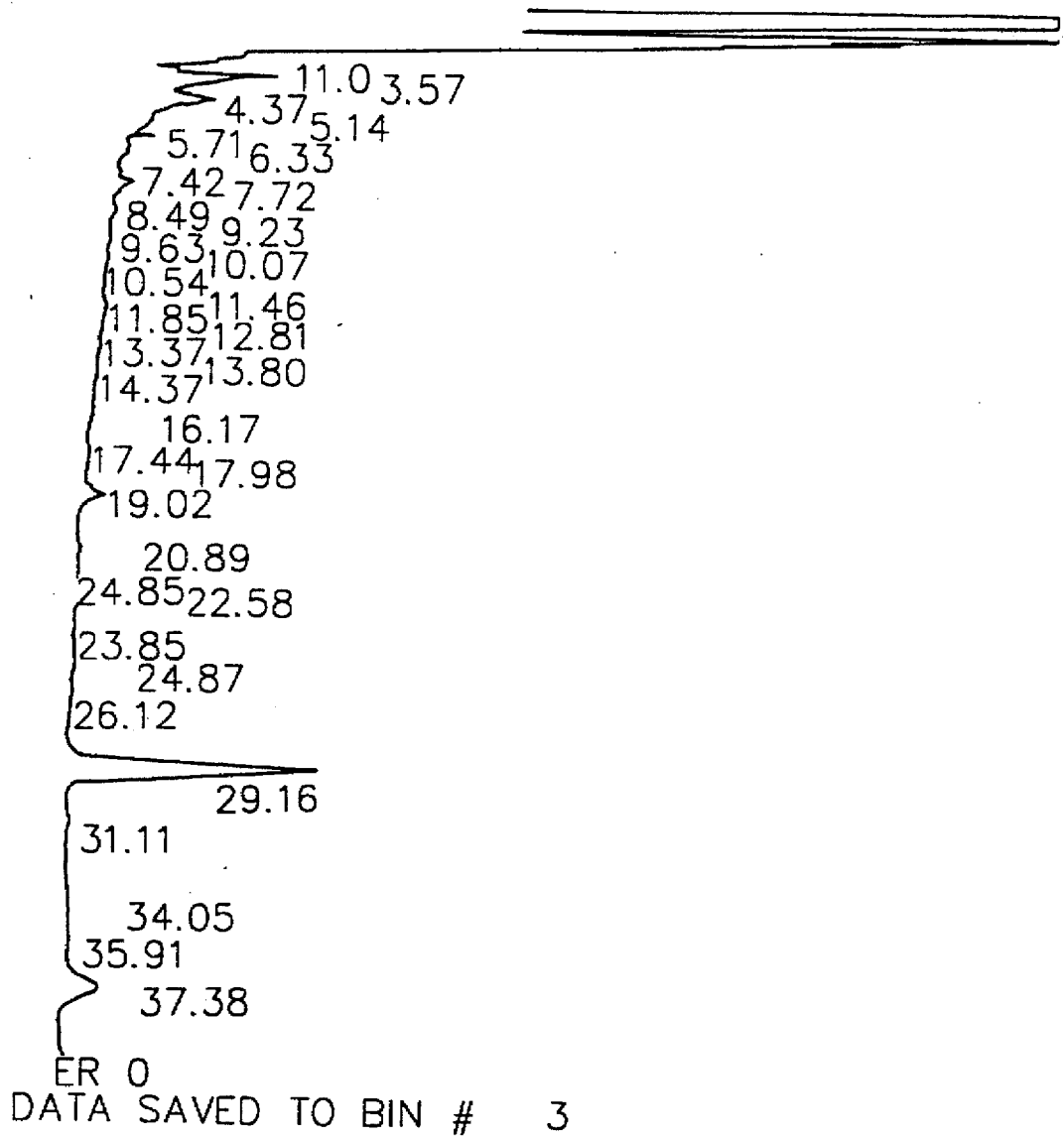
FIG. 4A is a chromatograph showing the production of cyclosporin by fermentation of Tolypocladium sp NRRL 8044 (ATCC 34921).

The cyclosporin concentration of broth was measured by High Performance Liquid Chromatography (HPLC) and the fermentation was stopped when cyclosporin production reached a maximum. The results of HPLC for Tolypocladium sp (Poli) are provided in FIGS. 3A and 3B; that for Tolypocladium sp NRRL 8044 (ATCC 34921) is is provided in FIGS. 4A and 4B.

As shown by the HPLC results, the cyclosporin A overall yield using Tolypocladium sp (Poli) was more than 2 g/liter. The cyclosporin A overall yield using Tolypocladium sp NRRL 8044 (ATCC 34921) was less than 0.5 g/liter. In published reports, fermentation of Tolypocladium sp. LEA3 is stated as producing up to 1.5 g/l of cyclosporin A after six days of fermentation, with the relative proportion of cyclosporin A up to 84% (U.S. Pat. No. 5,409,816).

The foregoing is illustrative of the present invention and is not to be construed as limiting thereof. The invention is defined by the following claims, with equivalents of the claims to be included therein.

That which is claimed is:

1. A biologically pure culture of the cyclosporin-producing microbe deposited as provisional accession number I-1714, Collection Nationale de Cultures de Microorganisms, Institut Pasteur.

* * * * *